(12) United States Patent
Cheng et al.

(10) Patent No.: US 8,753,605 B2
(45) Date of Patent: Jun. 17, 2014

(54) IMAGING PROBES, METHODS OF MAKING IMAGING PROBES, AND METHODS OF IMAGING

(75) Inventors: Zhen Cheng, Mountain View, CA (US); Sanjiv Sam Gambhir, Portola Valley, CA (US); Zheng Miao, Union City, CA (US); Hongguang Liu, Palo Alto, CA (US); Gang Ren, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 311 days.

(21) Appl. No.: 13/199,428

(22) Filed: Aug. 30, 2011

(65) Prior Publication Data

US 2012/0052009 A1    Mar. 1, 2012

Related U.S. Application Data

(60) Provisional application No. 61/378,510, filed on Aug. 31, 2010.

(51) Int. Cl.
| | |
|---|---|
| *A61K 51/00* | (2006.01) |
| *A61M 36/14* | (2006.01) |
| *A61K 49/00* | (2006.01) |
| *A61K 38/16* | (2006.01) |
| *A61K 49/14* | (2006.01) |
| *A61K 51/08* | (2006.01) |

(52) U.S. Cl.
CPC .............. *A61K 49/0004* (2013.01); *A61K 38/16* (2013.01); *A61K 49/0008* (2013.01); *A61K 49/14* (2013.01); *A61K 51/08* (2013.01); *A61K 51/088* (2013.01)
USPC ....... 424/1.89; 424/1.11; 424/1.65; 424/1.81; 424/1.85; 424/9.1; 424/9.2

(58) Field of Classification Search
CPC ........... A61K 2121/00; A61K 2123/00; A61K 51/0497; A61K 51/088; A61K 51/00; A61K 51/02; A61K 51/04; A61K 51/06; A61K 51/08; A61K 38/00; A61K 38/16; A61K 49/12; A61K 49/14; A61K 49/004; A61K 49/0008; A61K 49/00; A61K 49/0002; A61K 49/001; A61K 49/0013; A61K 49/0017; A61K 49/10; C07K 14/00
USPC ........... 424/1.11, 1.65, 1.69, 1.81, 1.85, 1.89, 424/9.1, 9.2, 9.3, 9.4, 9.5, 9.6, 9.7, 9.8; 514/1, 1.1; 530/300, 317, 324, 333, 530/338
See application file for complete search history.

(56) References Cited

U.S. PATENT DOCUMENTS

| | | | |
|---|---|---|---|
| 6,126,917 | A | 10/2000 | Mishani et al. |
| 7,527,942 | B2 | 5/2009 | Carey et al. |
| 7,597,876 | B2 | 10/2009 | McBride et al. |
| 7,696,320 | B2 | 4/2010 | Ignatovich et al. |

OTHER PUBLICATIONS

Miao et al, Journal of Biomedical Optics, 2010, 15(3), pp. 036007/1-036007/7.*
Miao et al, Bioconjugate Chem., 2010, 21(5), pp. 947-954.*

* cited by examiner

*Primary Examiner* — D L Jones
(74) *Attorney, Agent, or Firm* — Thomas|Horstemeyer, LLP (57) ABSTRACT

In accordance with the purpose(s) of the present disclosure, as embodied and broadly described herein, embodiments of the present disclosure, in one aspect, relate to methods of detecting the over-expression of epidermal growth factor receptor (EGFR) in a subject or sample, methods of diagnosing the presence of one or more angiogenesis related diseases or related biological events in a subject or sample, method of monitoring the progress of one or more angiogenesis related diseases or related biological events in a subject or sample, a $^{18}F$-FBEM-CYS-$Z_{EGFR:1907}$ probe, compositions including a $^{18}F$-FBEM-CYS-$Z_{EGFR:1907}$ probe, and pharmaceutical compositions including a $^{18}F$-FBEM-CYS-$Z_{EGFR:1907}$ probe and the like.

8 Claims, 6 Drawing Sheets
(5 of 6 Drawing Sheet(s) Filed in Color)

```
                        SEQUENCE LISTING

<160> NUMBER OF SEQ ID NOS: 1

<210> SEQ ID NO 1
<211> LENGTH: 58
<212> TYPE: PRT
<213> ORGANISM: Artificial Sequence
<220> FEATURE:
<223> OTHER INFORMATION: Chemically synthesized peptide probe

<400> SEQUENCE: 1

Val Asp Asn Lys Phe Asn Lys Glu Met Trp Ala Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                  45

Lys Lys Leu Asn Asp Ala Gln Ala Pro Lys
    50                  55
```

IMAGING PROBES, METHODS OF MAKING IMAGING PROBES, AND METHODS OF IMAGING

CROSS-REFERENCE TO RELATED APPLICATION

This application claims priority to U.S. provisional application entitled "IMAGING PROBES, METHODS OF MAKING IMAGING PROBES, AND METHODS OF IMAGING," having Ser. No. 61/378,510, filed on Aug. 31, 2010, which is entirely incorporated herein by reference.

STATEMENT OF GOVERNMENTAL SUPPORT

This invention was made with government support under grant number P50 CA114747, awarded by the National cancer institute of the United States government. The government has certain rights in the invention.

BACKGROUND

Epidermal growth factor receptor 1 (EGFR) is a transmembrane protein belonging to the ErbB receptor kinase family. Overexpression of EGFR has been frequently detected in a wide range of human tumors, for examples: small cell lung cancer, small cell carcinoma of the head and neck, esophageal cancer, gastric cancer, gliomas, colon cancer, pancreas cancer, breast cancer, ovary cancer, bladder cancer, kidneys cancer, prostate cancer, etc. Cetuximab, Lapatinib, Gefitinib, and Erlotinib have shown clinical benefits to lung, colorectal, pancreatic and breast cancer patients by targeting over-expressed/activated EGFR. Furthermore, increasing evidence has demonstrated that there is a correlation between EGFR overexpression and tumor metastasis formation, therapy resistance, poor prognosis and short survival for some cancer types. It has been found that EGFR expression level is a strong prognostic indicator for head and neck, ovarian, cervical, bladder and esophageal cancer. Therefore, EGFR has become an attractive target for cancer molecular imaging and therapy.

A variety of small molecules based upon EGFR substrates and EGF have been labeled with different radionuclides for molecular imaging of EGFR expression and activity. However the small molecules and EGF based probes generally show rapid blood clearance and very low tumor uptake, thus the imaging quality is poor. Radiolabeled monoclonal antibodies (MAbs) against EGFR demonstrate good tumor uptakes, but the tumors can only be visualized at several hours or even days after injection of the probes because of both the slow tumor targeting ability and slow clearance of the radiolabeled MAbs. Thus, there is a need to find alternative imaging moieties.

SUMMARY

In accordance with the purpose(s) of the present disclosure, as embodied and broadly described herein, embodiments of the present disclosure, in one aspect, relate to methods of detecting the over-expression of epidermal growth factor receptor (EGFR) in a subject or sample, methods of diagnosing the presence of one or more angiogenesis related diseases or related biological events in a subject or sample, method of monitoring the progress of one or more angiogenesis related diseases or related biological events in a subject or sample, a $^{18}$F-FBEM-CYS-$Z_{EGFR:1907}$ probe, compositions including a $^{18}$F-FBEM-CYS-$Z_{EGFR:1907}$ probe, pharmaceutical compositions including a $^{18}$F-FBEM-CYS-$Z_{EGFR:1907}$ probe, and the like.

In an embodiment, one method, among others, of detecting the over-expression of epidermal growth factor receptor (EGFR) in a subject includes: administering to the subject a $^{18}$F-FBEM-CYS-$Z_{EGFR:1907}$ probe, wherein $^{18}$F-FBEM is N-2-(4-$^{18}$F-fluorobenzamido)ethyl-maleimide), wherein $Z_{EGFR:1907}$ is SEQ ID NO: 1, and CYS is cysteine; imaging at least a portion of the subject; and detecting the $^{18}$F-FBEM-CYS-$Z_{EGFR:1907}$ probe, wherein the location of the $^{18}$F-FBEM-CYS-$Z_{EGFR:1907}$ probe corresponds to the over-expression of the EGFR.

In an embodiment, one method, among others, of diagnosing the presence of one or more angiogenesis related diseases or related biological events in a subject includes: administering to the subject a $^{18}$F-FBEM-CYS-$Z_{EGFR:1907}$ probe, wherein $^{18}$F-FBEM is N-2-(4-$^{18}$F-fluorobenzamido)ethyl-maleimide), wherein $Z_{EGFR:1907}$ is SEQ ID NO: 1, and CYS is cysteine; imaging at least a portion of the subject; and detecting the $^{18}$F-FBEM-CYS-$Z_{EGFR:1907}$ probe, wherein the location of the $^{18}$F-FBEM-CYS-$Z_{EGFR:1907}$ probe corresponds to the over-expression of the EGFR, wherein over-expression of EGFR corresponds to an angiogenesis related disease or related biological event.

In an embodiment, one method, among others, of diagnosing the presence of one or more angiogenesis related diseases or related biological events in a sample includes: contacting or administering to the sample a $^{18}$F-FBEM-CYS-$Z_{EGFR:1907}$ probe, wherein $^{18}$F-FBEM is N-2-(4-$^{18}$F-fluorobenzamido) ethyl-maleimide), wherein $Z_{EGFR:1907}$ is SEQ ID NO: 1, and CYS is cysteine; imaging at least a portion of the sample; and detecting the $^{18}$F-FBEM-CYS-$Z_{EGFR:1907}$ probe, wherein the location of the $^{18}$F-FBEM-CYS-$Z_{EGFR:1907}$ probe corresponds to the over-expression of the EGFR, wherein over-expression of EGFR corresponds to an angiogenesis related disease or related biological event.

In an embodiment, one method, among others, of monitoring the progress of one or more angiogenesis related diseases or related biological events in a subject includes: contacting or administering to the subject a $^{18}$F-FBEM-CYS-$Z_{EGFR:1907}$ probe, wherein $^{18}$F-FBEM is N-2-(4-$^{18}$F-fluorobenzamido) ethyl-maleimide), wherein $Z_{EGFR:1907}$ is SEQ ID NO: 1, and CYS is cysteine; imaging at least a portion of the subject; and detecting the $^{18}$F-FBEM-CYS-$Z_{EGFR:1907}$ probe, wherein the location of the 18F-FBEM-CYS-$Z_{EGFR:1907}$ probe corresponds to the over-expression of the EGFR, wherein over-expression of EGFR corresponds to an angiogenesis related disease or related biological event, wherein the size of the location is monitored over time.

In an embodiment, one method, among others, of monitoring the progress of one or more angiogenesis related diseases or related biological events in a sample includes: contacting or administering to the sample a $^{18}$F-FBEM-CYS-$Z_{EGFR:1907}$ probe, wherein $^{18}$F-FBEM is N-2-(4-$^{18}$F-fluorobenzamido) ethyl-maleimide), wherein $Z_{EGFR:1907}$ is SEQ ID NO: 1, and CYS is cysteine; imaging at least a portion of the sample; and detecting the $^{18}$F-FBEM-CYS-$Z_{EGFR:1907}$ probe, wherein the location of the 18F-FBEM-CYS-$Z_{EGFR:1907}$ probe corresponds to the over-expression of the EGFR, wherein over-expression of EGFR corresponds to an angiogenesis related disease or related biological event, wherein the size of the location is monitored over time.

In an embodiment, a probe, among others, includes a $^{18}$F-FBEM-CYS-$Z_{EGFR:1907}$ probe, wherein $^{18}$F-FBEM is N-2-(4-$^{18}$F-fluorobenzamido)ethyl-maleimide), wherein $Z_{EGFR:1907}$ is SEQ ID NO: 1, and CYS is cysteine.

In an embodiment, a composition, among others, includes: a $^{18}$F-FBEM-CYS-$Z_{EGFR:1907}$ probe, wherein $^{18}$F-FBEM is N-2-(4-$^{18}$F-fluorobenzamido)ethyl-maleimide), wherein $Z_{EGFR:1907}$ is SEQ ID NO: 1, and CYS is cysteine.

In an embodiment, a pharmaceutical composition, among others, includes: a pharmaceutical carrier and an effective dose of a $^{18}$F-FBEM-CYS-$Z_{EGFR:1907}$ probe, wherein $^{18}$F-FBEM is N-2-(4-$^{18}$F-fluorobenzamido)ethyl-maleimide), wherein $Z_{EGFR:1907}$ is SEQ ID NO: 1, and CYS is cysteine.

Other structures, methods, features, and advantages of the present disclosure will be, or become, apparent to one with skill in the art upon examination of the following drawings and detailed description. It is intended that all such additional structures, methods, features, and advantages be included within this description, be within the scope of the present disclosure, and be protected by the accompanying claims.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

The patent or application file contains at least one drawing executed in color. Copies of this patent or patent application publication with color drawing(s) will be provided by the Office upon request and payment of the necessary fee.

FIG. 1.1 illustrates the synthesis of $^{18}$F-FBEM-CYS-$Z_{EGFR:1907}$.

FIG. 1.2 illustrates a $^{18}$F-FBEM-CYS-$Z_{EGFR:1907}$ (1~250 µg dose, 60 µCi) microPET image of mice bearing EGFR overexpression A431 tumor xenograft at 0.1 and 3 h.p.i. (top: coronal images; bottom: transverse images) (T: tumor, L, liver, and K, kidney).

FIG. 1.3 illustrates a comparison of microPET imaging of mice bearing A431 tumor with $^{18}$F-FBEM-CYS-$Z_{EGFR:1907}$ (50 µg dose, 60 µCi) and $^{18}$F-FDG (90 µCi). Arrows were pointed at tumors.

FIG. 1.4 illustrates the micro PET imaging of mice bearing head and neck cancer tumor before and after anti-tumor drug treatment. 50~70 µCi of $^{18}$F-FBEM-CYS-$Z_{EGFR:1907}$ was injected into each mouse. Imaging was acquired 0.5 h, 1 h and 3 h post-injection. Arrows were pointed at tumors.

FIG. 2.1 illustrates the decay corrected coronal microPET images of a nu/nu mouse bearing human ovarian/breast tumor xenograft (tumor indicated by yellow arrows) at 24 h after tail vein injection of $^{64}$Cu-DOTA-$Z_{EGFR:1907}$.

FIG. 2.2 illustrates the cell uptake of $^{64}$Cu-DOTA-$Z_{EGFR:1907}$ in SUM159 cells over time at 37° C. vs. 4° C.

FIG. 2.3 illustrates the decay corrected coronal microPET images of a nu/nu mouse bearing SUM159 (indicated by yellow arrows) after tail vein injection of $^{64}$Cu-DOTA-$Z_{EGFR:1907}$ (Top) or $^{18}$F-FBEM-$Z_{EGFR:1907}$ (Bottom).

FIG. 2.4 illustrates the biodistribution results for $^{64}$Cu-DOTA-$Z_{EGFR:1907}$ in nude mice bearing subcutaneously xenotransplanted SUM159 human breast cancer.

FIG. 2.5 illustrates the tumor-to-normal-tissue ratios for $^{64}$Cu-DOTA-$Z_{EGFR:1907}$ in nude mice bearing subcutaneously xenotransplanted SUM159 human breast cancer.

FIG. 2.6 illustrates the decay corrected coronal microPET images of a nu/nu mouse bearing MDA-MB-231 (Top) or SUM159 (Bottom) after tail vein injection of $^{64}$Cu-DOTA-$Z_{EGFR:1907}$.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, biochemistry, biology, molecular biology, molecular imaging, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

By "administration" is meant introducing a probe (also referred to as the "imaging agent") of the present disclosure into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the probe of the present disclosure is defined as an amount sufficient to yield an acceptable image using equipment that is available for clinical use. A detectably effective amount of the probe of the present disclosure may be administered in more than one injection. The detectably effective amount of the probe of the present disclosure can vary according to factors such as the degree of susceptibility of the individual, the age, sex, and weight of the individual, idiosyncratic responses of the individual, and the like. Detectably effective amounts of the probe of the present disclosure can also vary according to instrument and film-related factors. Optimization of such factors is well within the level of skill in the art.

As used herein, the term "host" or "subject" includes humans and mammals (e.g., cats, dogs, horses, etc.). Typical hosts to which embodiments of the present disclosure may be administered can include mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host. The term "living host" refers to a host or organism noted above that are alive and are not dead. The term "living host" refers to the entire host or organism and not just a part excised (e.g., a liver or other organ) from the living host.

The term "sample" can refer to a tissue sample, cell sample, a fluid sample, and the like. The sample may be taken from a subject. The tissue sample can include hair (including roots), buccal swabs, blood, saliva, semen, tumor, muscle, organ, or from any internal organs. The fluid may be, but is not limited to, urine, blood, ascites, pleural fluid, spinal fluid, and the like. The body tissue can include, but is not limited to, tumor, organ, skin, muscle, endometrial, uterine, and cervical tissue. In the present disclosure, the source of the sample is not critical.

The phrase "effective amount" as used herein refers to that amount of an embodiment of the composition or pharmaceutical composition being administered that a detectable signal is produced.

The term "detectable" refers to the ability to detect a signal over the background signal.

The term "detectable signal" is a signal derived from noninvasive imaging techniques such as, but not limited to, positron emission tomography (PET) or single photon emission computed tomography (SPECT). The detectable signal is detectable and distinguishable from other background signals that may be generated from the subject. In other words, there is a measurable and statistically significant difference (e.g., a statistically significant difference is enough of a difference to distinguish among the acoustic detectable signal and the background, such as about 0.1%, 1%, 3%, 5%, 10%, 15%, 20%, 25%, 30%, or 40% or more difference between the detectable signal and the background) between detectable signal and the background. Standards and/or calibration curves can be used to determine the relative intensity of the detectable signal and/or the background.

Over-expression of epidermal growth factor receptor (EGFR) has been associated or linked with cancer. "Cancer", as used herein, shall be given its ordinary meaning, as a general term for diseases in which abnormal cells divide without control. In particular, cancer refers to angiogenesis related cancer. Cancer cells can invade nearby tissues and can spread through the bloodstream and lymphatic system to other parts of the body.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

General Discussion

Embodiments of the present disclosure provide for a $^{18}$F-FBEM-CYS-$Z_{EGFR:1907}$ (where $^{18}$F-FBEM is N-2-(4-$^{18}$F-fluorobenzamido)ethyl-maleimide), where $Z_{EGFR:1907}$ is SEQ ID NO: 1, and CYS is cysteine) probe, methods of making a $^{18}$F-FBEM-CYS-$Z_{EGFR:1907}$ probe, pharmaceutical compositions including a $^{18}$F-FBEM-CYS-$Z_{EGFR:1907}$ probe, methods of using a $^{18}$F-FBEM-CYS-$Z_{EGFR:1907}$ probe, methods of diagnosing, localizing, monitoring, and/or assessing angiogenesis related diseases, cancers, tumors, precancerous cells, and related biological events, or EGFR over-expression using a $^{18}$F-FBEM-CYS-$Z_{EGFR:1907}$ probe, kits for diagnosing, localizing, monitoring, and/or assessing angiogenesis related diseases, cancers, tumors, precancerous cells, and related biological events, or EGFR over-expression using a $^{18}$F-FBEM-CYS-$Z_{EGFR:1907}$ probe, and the like. In particular, the present disclosure includes methods relating to non-invasive imaging (e.g., positron emission tomography (PET) imaging) using a $^{18}$F-FBEM-CYS-$Z_{EGFR:1907}$ probe in vivo.

Embodiments of the present disclosure include methods for imaging tissue, cells, or a subject, that includes contacting with or administering to a tissue, cells, or subject, a $^{18}$F-FBEM-CYS-$Z_{EGFR:1907}$ probe, and imaging with a PET imaging system. The imaging can be performed in vivo and/or in vitro. In particular, embodiments of the present disclosure can be used to image angiogenesis related diseases, such as cancers or tumors, or related biological events. In an embodiment, $^{18}$F-FBEM-CYS-$Z_{EGFR:1907}$ probes can be used to image EGFR over-expression. In this regard, the tissue, cells, or subject, can be tested to determine if the tissue, cells, or subject includes an angiogenesis related disease or related biological events, monitor the progression (or regression) of the disease, assess the response of the disease to treatment, image or monitor the over-expression of EGFR, and the like. In an embodiment, the tissue or cells can be within a subject or have been removed from a subject.

The $^{18}$F-FBEM-CYS-$Z_{EGFR:1907}$ probe can be imaged using imaging systems such as positron emission tomography (PET) imaging systems, single photon emission computed tomography (SPECT), and the like. In an embodiment, PET imaging is a preferred embodiment.

The $^{18}$F-FBEM-CYS-$Z_{EGFR:1907}$ probe includes a label, $^{18}$F, that can be used to detect, image, or otherwise identify the $^{18}$F-FBEM-CYS-$Z_{EGFR:1907}$ probe, quantify the amount of $^{18}$F-FBEM-CYS-$Z_{EGFR:1907}$ probe, determine the location of the $^{18}$F-FBEM-CYS-$Z_{EGFR:1907}$ probe (e.g., in imaging), and combinations thereof. Fluorine-18 ($t_{1/2}$=109.7 min; $\beta^+$, 99%) is an ideal short-lived PET isotope for labeling small molecules.

Figure 11:
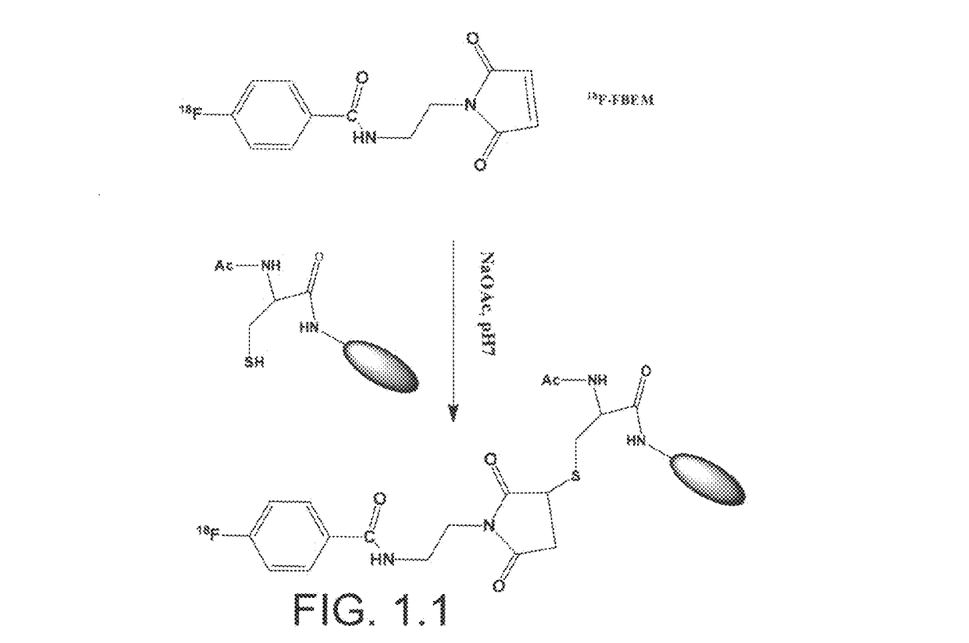

FIG. 1 illustrates an embodiments of the $^{18}$F-FBEM-CYS-$Z_{EGFR:1907}$ probe and a method of making the $^{18}$F-FBEM-CYS-$Z_{EGFR:1907}$ probe. N-2-(4-$^{18}$F-fluorobenzamido)ethyl-maleimide ($^{18}$F-FBEM) can be conjugated with Ac-Cys-$Z_{EGFR:1907}$ according to the synthesis shown in FIG. 2. Additional details regarding the $^{18}$F-FBEM-CYS-$Z_{EGFR:1907}$ probe and the method of making the $^{18}$F-FBEM-CYS-$Z_{EGFR:1907}$ probe are described in Example 1.

Methods of Use

Embodiments of this disclosure include, but are not limited to: methods of imaging tissue, cells, or a subject using the $^{18}$F-FBEM-CYS-$Z_{EGFR:1907}$ probe; methods of imaging an angiogenesis related disease (e.g., cancer or tumor) or related biological events, or over-expression of EGFR using the $^{18}$F-FBEM-CYS-$Z_{EGFR:1907}$ probe; methods of diagnosing an angiogenesis related disease or related biological events or over-expression of EGFR using the $^{18}$F-FBEM-CYS-$Z_{EGFR:1907}$ probe; methods of monitoring the progress of an angiogenesis related disease or related biological events or over-expression of EGFR using the $^{18}$F-FBEM-CYS-$Z_{EGFR:1907}$ probe, and the like.

Embodiments of the present disclosure can be used to image, detect, study, monitor, evaluate, assess, and/or screen, the angiogenesis related diseases or related biological events or over-expression of EGFR in vivo or in vitro using the $^{18}$F-FBEM-CYS-$Z_{EGFR:1907}$ probe.

In general, the $^{18}$F-FBEM-CYS-$Z_{EGFR:1907}$ probe can be used in imaging angiogenesis related diseases, and, in particular, over-expression of EGFR. For example, the $^{18}$F-FBEM-CYS-$Z_{EGFR:1907}$ probe is provided or administered to a subject in an amount effective to result in uptake of the $^{18}$F-FBEM-CYS-$Z_{EGFR:1907}$ probe into the angiogenesis related disease or tissue of interest. The subject is then introduced to an appropriate imaging system (e.g., PET system) for a certain amount of time. The angiogenesis related disease that takes up the $^{18}$F-FBEM-CYS-$Z_{EGFR:1907}$ probe could be detected using the imaging system. The location of the detected signal from the $^{18}$F-FBEM-CYS-$Z_{EGFR:1907}$ probe can be correlated with the location of the angiogenesis related diseases, and, in particular, over-expression of EGFR.

The steps of this method can be repeated at determined intervals so that the location and/or size of the disease or over-expression of EGFR can be monitored as a function of time and/or treatment. In particular, the 18F-FBEM-CYS-$Z_{EGFR:1907}$ probe can find use in a host undergoing chemotherapy or other treatment (e.g., using a drug), to aid in visualizing the response of a disease or tumor to the treatment. In this embodiment, the $^{18}$F-FBEM-CYS-$Z_{EGFR:1907}$ probe is typically visualized and sized prior to treatment, and periodically during chemotherapy to monitor the tumor size.

Embodiments of the $^{18}$F-FBEM-CYS-$Z_{EGFR:1907}$ probe also finds use as a screening tool in vitro to select compounds for use in treating angiogenesis related diseased tissue or cells, or over-expression of EGFR. The angiogenesis related disease could be easily monitored by incubating the cells with the disease with the $^{18}$F-FBEM-CYS-$Z_{EGFR:1907}$ probe during or after incubation with one or more candidate drugs. The ability of the drug compound to affect the disease can be imaged over time using the $^{18}$F-FBEM-CYS-$Z_{EGFR:1907}$ probe.

It should be noted that the amount effective, for the methods described herein, to result in the uptake of $^{18}$F-FBEM-CYS-$Z_{EGFR:1907}$ probe into the cells or tissue of interest will depend upon a variety of factors, including for example, the age, body weight, general health, sex, and diet of the host; the time of administration; the route of administration; the rate of excretion of the specific probe employed; the duration of the treatment; the existence of other drugs used in combination or coincidental with the specific composition employed; the type of method (e.g., imaging, diagnosing, monitoring, etc.) and like factors well known in the medical arts.

Kits

The present disclosure also provides packaged compositions or pharmaceutical compositions comprising a pharmaceutically acceptable carrier and $^{18}$F-FBEM-CYS-$Z_{EGFR:1907}$ probe of the disclosure. In certain embodiments, the packaged compositions or pharmaceutical composition includes the reaction precursors to be used to generate the $^{18}$F-FBEM-CYS-$Z_{EGFR:1907}$ probe according to the present disclosure. Other packaged compositions or pharmaceutical compositions provided by the present disclosure further include indicia including at least one of: instructions for using the $^{18}$F-FBEM-CYS-$Z_{EGFR:1907}$ probe to image a host, or host samples (e.g., cells or tissues), which can be used as an indicator of conditions including, but not limited to, angiogenesis related disease and biological related events or overexpression of EGFR.

Embodiments of this disclosure encompass kits that include, but are not limited to, the 18F-FBEM-CYS-$Z_{EGFR:1907}$ probe and directions (written instructions for their use). The components listed above can be tailored to the particular biological event to be monitored as described herein. The kit can further include appropriate buffers and reagents known in the art for administering various combinations of the components listed above to the host cell or host organism. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like.

Dosage Forms

Embodiments of the present disclosure can be included in one or more of the dosage forms mentioned herein. Unit dosage forms of the pharmaceutical compositions (the "composition" includes at least the $^{18}$F-FBEM-CYS-$Z_{EGFR:1907}$ probe) of this disclosure may be suitable for oral, mucosal (e.g., nasal, sublingual, vaginal, buccal, or rectal), parenteral (e.g., intramuscular, subcutaneous, intravenous, intra-arterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure typically vary depending on their use. For example, a parenteral dosage form may contain smaller amounts of the active ingredient than an oral dosage form used to treat the same condition or disorder. These and other ways in which specific dosage forms encompassed by this disclosure vary from one another will be readily apparent to those skilled in the art (See, e.g., *Remington's Pharmaceutical Sciences,* 18th ed., Mack Publishing, Easton, Pa. (1990)).

Typical compositions and dosage forms of the compositions of the disclosure can include one or more excipients. Suitable excipients are well known to those skilled in the art of pharmacy or pharmaceutics, and non-limiting examples of suitable excipients are provided herein. Whether a particular excipient is suitable for incorporation into a composition or dosage form depends on a variety of factors well known in the art including, but not limited to, the way in which the dosage form will be administered to a patient. For example, oral dosage forms, such as tablets or capsules, may contain excipients not suited for use in parenteral dosage forms. The suitability of a particular excipient may also depend on the specific active ingredients in the dosage form. For example, the decomposition of some active ingredients can be accelerated by some excipients, such as lactose, or by exposure to water. Active ingredients that include primary or secondary amines are particularly susceptible to such accelerated decomposition.

The disclosure encompasses compositions and dosage forms of the compositions of the disclosure that can include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate, or organic acids. An exemplary solubility modulator is tartaric acid.

"Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

Embodiments of the present disclosure include pharmaceutical compositions that include the $^{18}$F-FBEM-CYS-$Z_{EGFR:1907}$ probe, pharmaceutically acceptable salts thereof, with other chemical components, such as physiologically acceptable carriers and excipients. One purpose of a pharmaceutical composition is to facilitate administration of $^{18}$F-FBEM-CYS-$Z_{EGFR:1907}$ probe to an organism.

Embodiments of the present disclosure may salts and these salts are within the scope of the present disclosure. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when an embodiment of the present disclosure contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an active compound may be formed, for example, by reacting an active compound with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the disclosure are also contemplated herein. Solvates of the compounds are preferably hydrates.

The amounts and specific type of active ingredient (18F-FBEM-CYS-$Z_{EGFR:1907}$ probe) in a dosage (e.g., pharmaceutically effective amount) form may differ depending on various factors. It will be understood, however, that the total daily usage of the compositions of the present disclosure will be decided by the attending physician or other attending professional within the scope of sound medical judgment. The specific effective dose level for any particular host will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts. For example, it is well within the skill of the art to start doses of the composition at levels lower than those required to achieve the desired effect and to gradually increase the dosage until the desired effect is achieved.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

FIG. 1.1 illustrates an illustrative synthesis for preparing a 18F-FBEM-CYS-$Z_{EGFR:1907}$ probe. The oval represents the EGFR Affibody peptide ($Z_{EGFR:1907}$), where CYS is bonded to V of the $Z_{EGFR:1907}$.

Ac-Cys-$Z_{EGFR:1907}$ (Ac-VDNKFNKEMWAAWEEIRN-LPNLNGWQMTAFIAS LVDDPSQSANLLAE-AKKLNDAQAPK-NH$_2$, from VDN . . . to . . . APK, is SEQ ID NO: 1 (VDNKFNKEMWAAWEEIRNLPNLNG-WQMTAFIASLVDDPSQSANLLAEAKKLNDA QAPK)) was synthesized on an automatic peptide synthesizer (CS Bio, CS 336X). Briefly, Rink Amide LS resin (200 mg, 40 µmol, Advanced ChemTech, 0.2 mmol/g loading) was swollen in N,N-dimethylformamide (DMF) for 30 min. Fmoc-protected amino acids were purchased from Novabiochem/EMD Chemicals Inc. Fmoc groups were removed with 20% piperidine in DMF. The aliquots of amino acids (0.20 mmol) were activated in a solution containing 0.20 mmol of HOBt and 0.5 M diisopropylcarbodiimide (DIC) in DMF. The small protein was N-terminal-acetylated by activation of acetic anhydride with HOBt/DIEA after deprotection of the Fmoc protection group of last amino acid residue. Peptide cleavage and deprotection were carried out by a 3-h incubation in a mixture of TFA/TIS/EDT/H$_2$O (94:2:2:2). The mixture was filtered, and the peptide in solution was precipitated with anhydrous diethyl ether. The resulting peptide was washed four times with ice-cold anhydrous diethyl ether, dried, and dissolved in 1 mM DTT. The peptide was purified by RP-HPLC on a C-18 column. Fractions were collected and lyophilized. The target product was characterized by ESI-MS and ready for use in the next step in the reaction.

No-carrier-added [18F]F$^-$ was obtained through the nuclear reaction $^{18}$O(p, n)$^{18}$F by irradiation of 95% $^{18}$O-enriched water with an 11 MeV proton beam. After the delivery of [$^{18}$F]F$^-$ from the cyclotron, the radioactivity was passed through a Sep-Pak light QMA cartridge to trap [18F]F$^-$. The Sep-Pak light QMA cartridge was pre-conditioned sequentially with 5 mL of 0.5M potassium bicarbonate, 10 mL of deionized water, and 10 mL of acetonitrile before use. The [$^{18}$F]F$^-$ was eluted with 1.5 mL of a solution prepared by mixing aqueous K$_2$CO$_3$ (0.11 g, 0.8 mmol in 1.0 mL of water) with Kryptofix 222 (K222) (0.60 g, 1.6 mmol in 19 mL of acetonitrile). The solvent was evaporated under a stream of nitrogen at 120° C. Azeotropic drying was repeated twice with 1 mL portions of MeCN to generate the anhydrous K222/K[$^{18}$F]F complex. Ethyl 4-(trimethylammonium triflate)benzoate (5.0 mg, 20 mmol) in anhydrous MeCN (1 mL) was added to the dried K222/K[18F]F and the mixture heated at 90° C. for 10 min to produce ethyl 4-[$^{18}$F]fluorobenzoate. The ethyl ester was subsequently hydrolyzed to form 4-[$^{18}$F]fluorobenzoate using 20 mL of tetrapropylammonium hydroxide (1.0M in water) at 120° C. for 3 min, and then the mixture azeotropically dried using MeCN (1 mL). Subsequently, a solution of N,N,N',N'-tetramethyl-O-(N-succinimidyl) uronium hexafluorophosphate (TSTU) (12 mg, 33 mmol) in MeCN (1 mL) was added and the solution heated at 90° C. for 5 min. After cooling, 5% aqueous acetic acid (9 mL) and water (15 mL) were added. The reaction mixture was passed through a Sep-pak C18 cartridge. The cartridge was washed with 10 mL 10% acetonitrile/water. Then the product was eluted by acetonitrile and dried by blowing argon. The specific activity of $^{18}$F-SFB was 100-200 GBq/µmol at the end of synthesis (EOS), as estimated by radio-HPLC. $^{18}$F-SFB in 200 µL of DMSO was added to ethylene-maleimide (1.5 mg, in 200 µL of DMSO) and 25 µL of DIPEA and reacted for 30 min at 50° C. After adding 30 µL of TFA to quench the reaction, the mixture was purified with semi-preparative HPLC, using the same elution gradient of 0-3 min, 5-65%; 3-33 min, 5-65%; 33-34 min, 65-85% and 34-36 min, 85%. The eluted fractions at 24 min containing the $^{18}$F-FBEM were then collected, combined, and dried using a rotary evaporator. $^{18}$F-FBEM was re-suspended in 200 µL of sodium acetate buffer (0.1M, pH 6) with 0.1% ascorbic acid and added to 100-200 µg of AC-Cys-$Z_{EGFR:1907}$. The mixture was incubated at room temperature for 30 min. Then the product $^{18}$F-FBEM-CYS-$Z_{EGFR:1907}$ was purified by PD-10 column. The 18F-FBME- is attached to the Cys residue of $Z_{EGFR:1907}$.

Figure 12:
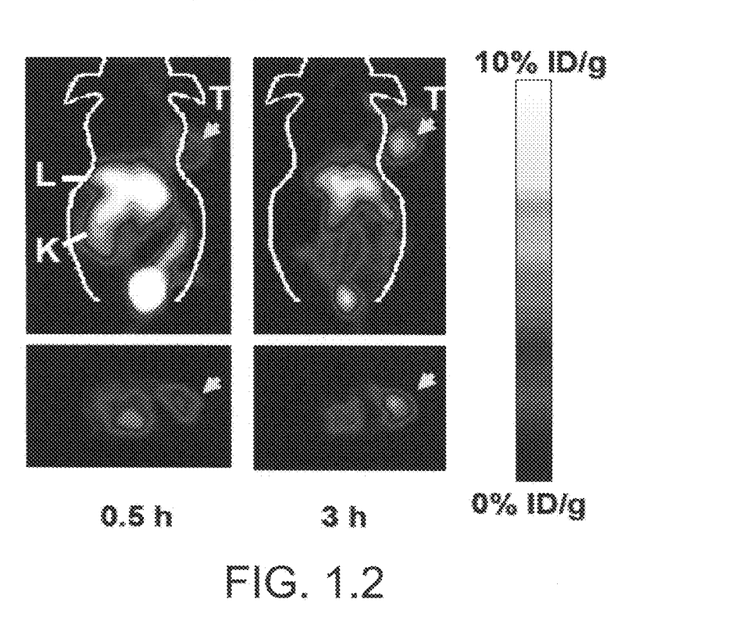

FIG. 1.2 illustrates microPET images of mice bearing A431 tumors to show over-expression of EGFR. Mice were injected with $^{18}$F-FBEM-CYS-$Z_{EGFR:1907}$ probes or $^{18}$F-FDG probes.

Figure 13:
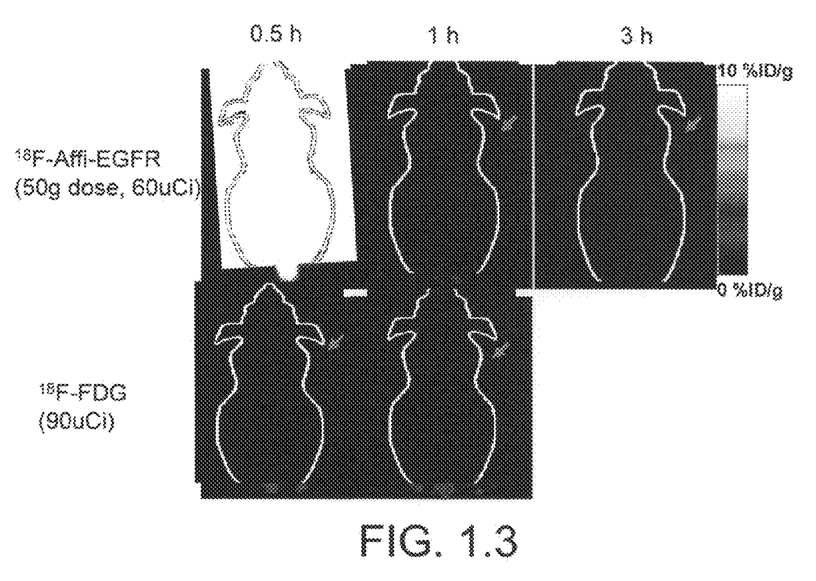

FIG. 1.3 illustrates the comparison of microPET imaging of mice bearing A431 tumor with $^{18}$F-FBEM-CYS-$Z_{EGFR:1907}$ (50 µg dose, 60 µCi) and $^{18}$F-FDG (90 µCi). Arrows were pointed at tumors.

PET imaging of tumor-bearing mice was performed on a microPET R4 rodent model scanner (Siemens Medical Solutions USA, Inc.). The mice bearing A431 tumor were injected with $^{18}$F-FBEM-CYS-$Z_{EGFR:1907}$ (1.85-2.59 MBq, 50-70 µCi, 2-3 µg) coinjected with 45 µg of cold Ac-Cys-$Z_{EGFR:1907}$ via the tail vein. Another group of mice bearing A431 tumor were injected with $^{18}$F-FDG (90 µCi). At different times after the injection, the mice were anesthetized with 2% isoflurane and placed in the prone position and near the center of the field of view of a microPET. The 3-min static scans were obtained, and the images were reconstructed by a two-dimensional ordered subsets expectation maximum (OSEM) algorithm. No background correction was performed. $^{18}$F-FBEM-CYS-$Z_{EGFR:1907}$ showed high uptake in tumor at all time-point while the imaging contrast is the best at 3 h post-injection. $^{18}$F-FDG has similar contrast to $^{18}$F-FBEM-CYS-$Z_{EGFR:1907}$ at early time point, but the tumor uptake is lower.

Figure 14:
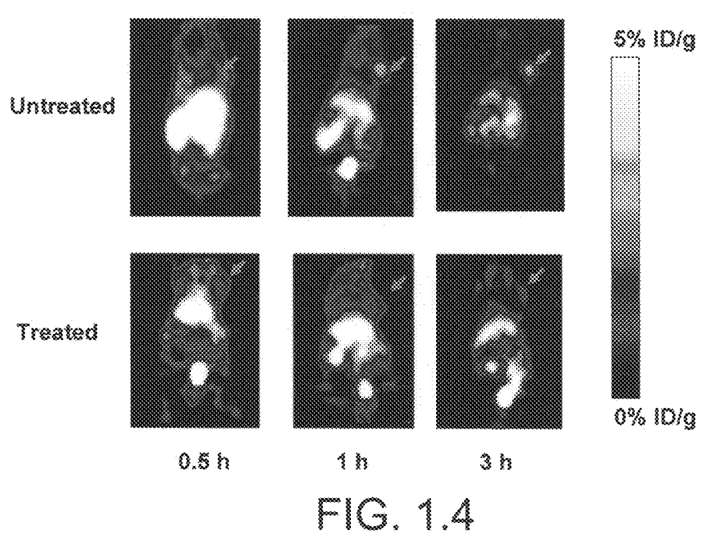

FIG. 1.4 illustrates microPET images of mice bearing head and neck tumors to show over-expression of EGFR. Mice were injected with $^{18}$F-FBEM-CYS-$Z_{EGFR:1907}$ probes.

PET imaging of tumor-bearing mice was performed on a microPET R4 rodent model scanner (Siemens Medical Solutions USA, Inc.). The mice bearing head and neck cancer were injected with $^{18}$F-FBEM-CYS-$Z_{EGFR:1907}$ (1.85-2.59 MBq, 50-70 µCi, 2-3 µg) spiked with cold Ac-Cys-$Z_{EGFR:1907}$ (45 µg) via the tail vein. For the treated group, mice were scanned three weeks after anti-cancer drug treatment. At different times after the injection, the mice were anesthetized with 2% isoflurane and placed in the prone position and near the center of the field of view of a microPET. The 3-min static scans were obtained, and the images were reconstructed by a two-dimensional ordered subsets expectation maximum (OSEM) algorithm. No background correction was performed. $^{18}$F-FBEM-CYS-$Z^{EGFR:1907}$ showed high uptake in head and neck tumor. After treatment, the growth of tumor was depressed and $^{18}$F-FBEM-CYS-$Z_{EGFR:1907}$ microPET imaging showed prohibition of EGFR over-expression in the tumor.

Example 2

Introduction

Triple Negative Breast Cancer (TNBC) represents a group of refractory breast cancer with aggressive clinical manifestations as well as poor prognosis. Epidermal growth factor receptor (EGFR) expression is strongly associated with TNBC progression and it may serve as a therapeutic target for TNBC. EGFR affibody has been developed to target EGFR with high binding affinity[1,2]. In this study, we aimed to characterize EGFR expression in TNBC mouse model using EGFR affibody based PET imaging.
Methodology Ac-Cys-$Z_{EGFR:1907}$ was chemically synthesized using a solid phase peptide synthesizer and then site-specifically conjugated with 1,4,7,10-tetraazacyclododecane-1,4,7,10-tetraacetic acid (DOTA) for radiolabeling or N-2-(4-$^{18}$F-fluorobenzamido)-ethyl]-maleimide ($^{18}$F-FBEM)[3]. The in vitro cell uptake study was performed using SUM159 cells. MicroPET imaging using $^{64}$Cu-DOTA-$Z_{EGFR:1907}$ or $^{18}$F-FBEM-$Z_{EGFR:1907}$ were evaluated in nude mice bearing subcutaneous MDA-MB-231 and SUM159 TNBC tumors. Biodistribution studies were performed to understand the in vivo pharmacokinetics of $Z_{EGFR:1907}$. Immunohistochemistry studies were performed to confirm imaging findings ex vivo (data not shown).
Results and Discussions Ac-Cys-$Z_{EGFR:1907}$ was successfully synthesized on an automatic peptide synthesizer and conjugated with DOTA.

A pilot study confirmed medium to high EGFR expressions in two TNBC models (MDA-MB-231 and SUM 159).

SUM 159 cells and tumors both showed decent uptake of $^{64}$Cu-DOTA-$Z_{EGFR:1907}$, consistent with the overexpression of EGFR in TNBC. Co-injection of 150 µg of EGFR affibody blocked the tumor uptake in vivo.

MicroPET imaging based upon $^{64}$Cu/$^{18}$F labeled Ac-Cys-$Z_{EGFR:1907}$ could be used to monitor EGFR expression in TNBC in vivo.

Figure 21:
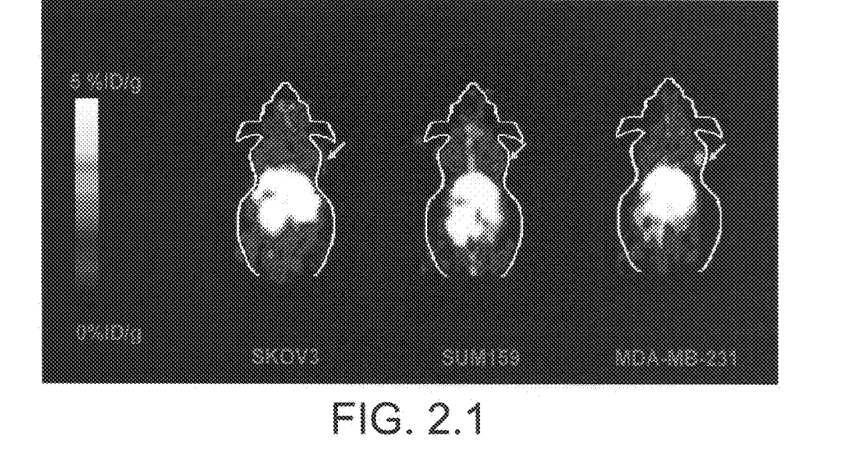

FIG. 2.1 illustrates the decay corrected coronal microPET images of a nu/nu mouse bearing human ovarian/breast tumor xenograft (tumor indicated by yellow arrows) at 24 h after tail vein injection of $^{64}$Cu-DOTA-CYS-$Z_{EGFR:1907}$.

Triple negative breast cancer (SUM 159 and MDA-MB-231) has shown higher uptake of $^{64}$Cu-DOTA-CYS-$Z_{EGFR:1907}$ while ovarian cancer SKOV3 has shown lower uptake of $^{64}$Cu-DOTA-CYS-$Z_{EGFR:1907}$. But there is a very high liver uptake and kidney uptake of the of $^{64}$Cu-DOTA-CYS-$Z_{EGFR:1907}$ and a toxicity limit because of long half life of Cu-64. Thus a fluorinated version of $Z_{EGFR:1907}$ will reduce the toxicity.

Figure 22:
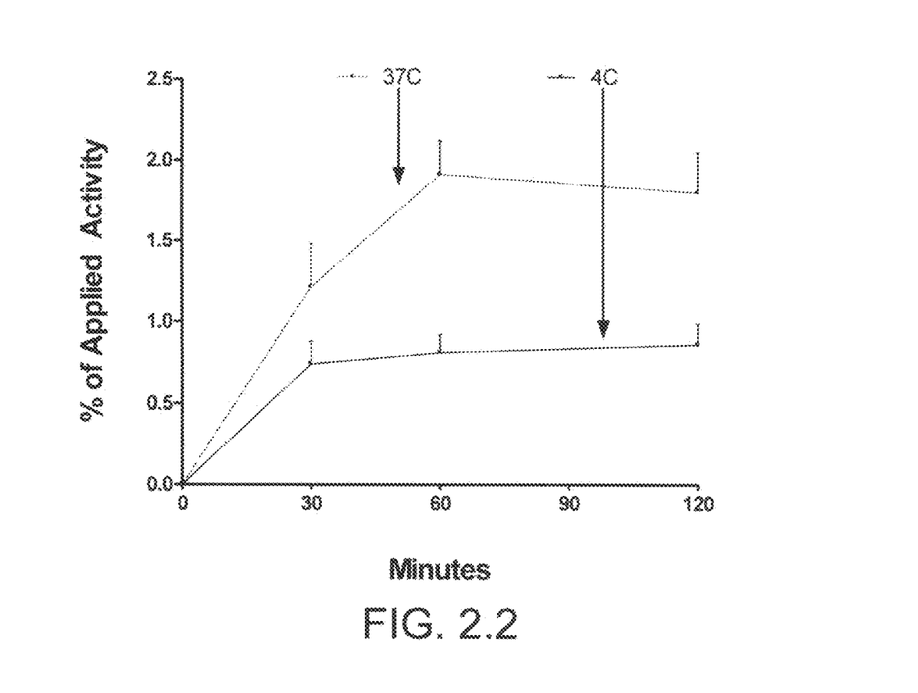

FIG. 2.2 illustrates the cell uptake of $^{64}$Cu-DOTA-CYS-$Z_{EGFR:1907}$ in SUM159 cells over time at 37° C. vs. 4° C.

Figure 23:
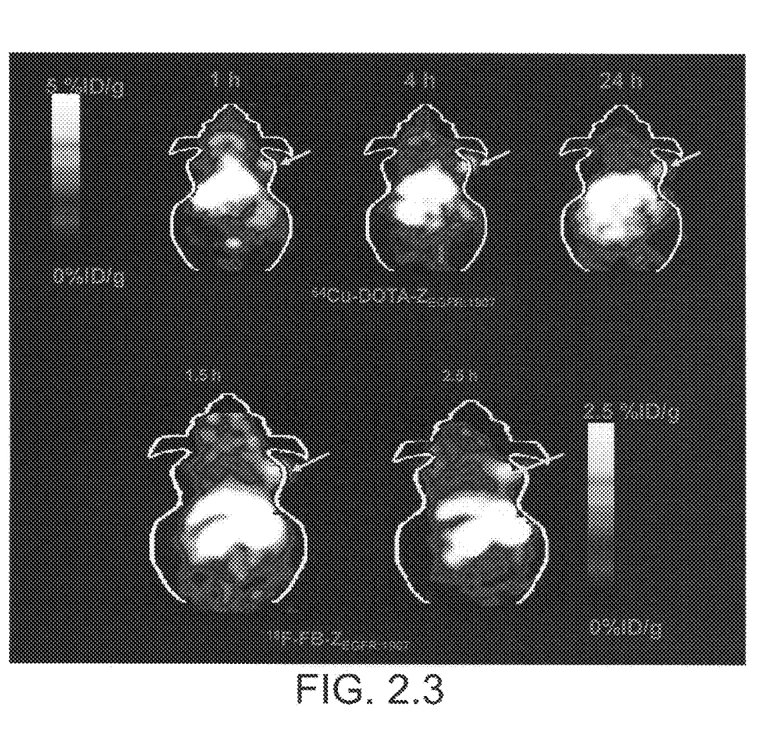

FIG. 2.3 illustrates the decay corrected coronal microPET images of a nu/nu mouse bearing SUM159 (indicated by yellow arrows) after tail vein injection of $^{64}$Cu-DOTA-CYS-$Z_{EGFR:1907}$ (Top) or $^{18}$F-FBEM-CYS-$Z_{EGFR:1907}$ (Bottom).

The fast accumulation of $^{18}$F-FBEM-CYS-$Z_{EGFR:1907}$ matches well with the short half life of F-18 (109 min). At as early as 1.5 h p.i., high contrast imaging has already been shown at tumor.

Figure 24:
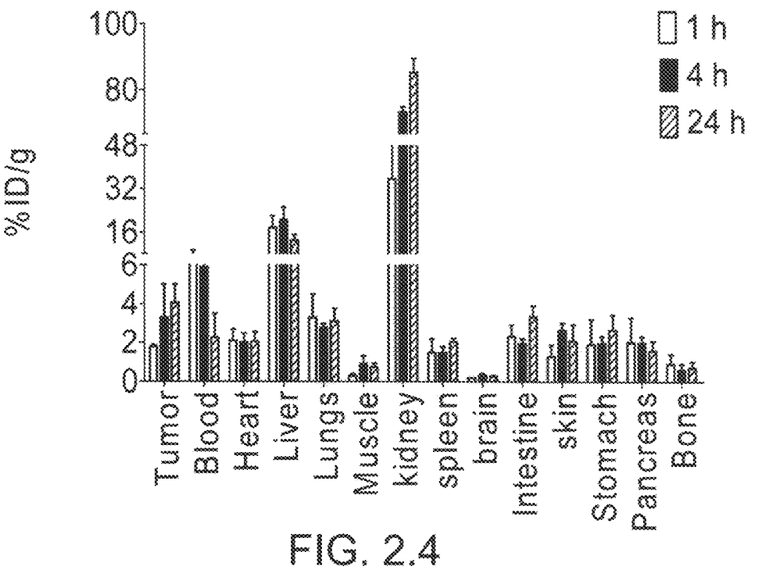

FIG. 2.4 illustrates the biodistribution results for $^{64}$Cu-DOTA-CYS-$Z_{EGFR:1907}$ in nude mice bearing subcutaneously xenotransplanted SUM159 human breast cancer.

Figure 25:
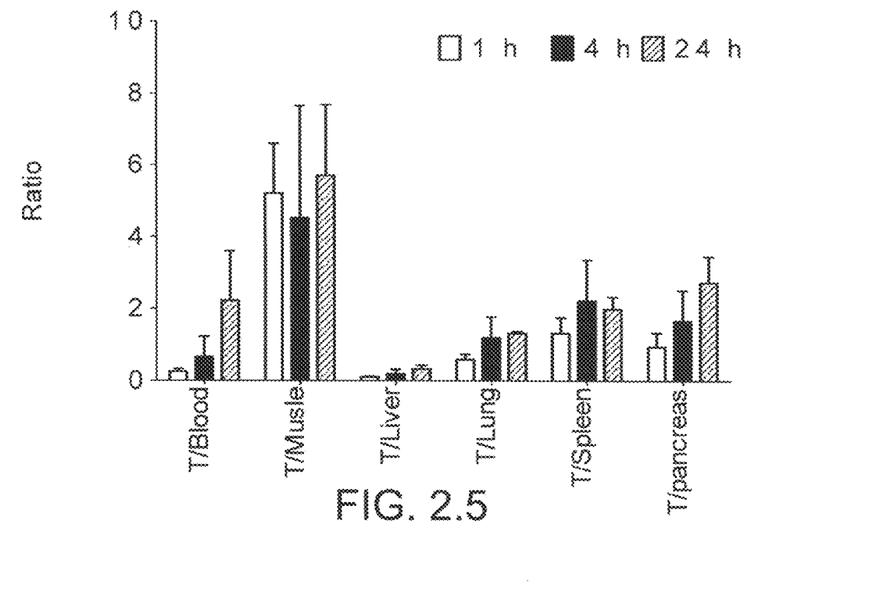

FIG. 2.5 illustrates the tumor-to-normal-tissue ratios for $^{64}$Cu-DOTA-CYS-$Z_{EGFR:1907}$ in nude mice bearing subcutaneously xenotransplanted SUM159 human breast cancer.

Tumor to normal organ/tissues ratios increased significantly with the increase of time, suggesting the good retention of $Z_{EGFR:1907}$ in the tumor and potential for dual modality PET/CT, PET/MRI imaging in a large time windows.

Figure 26:
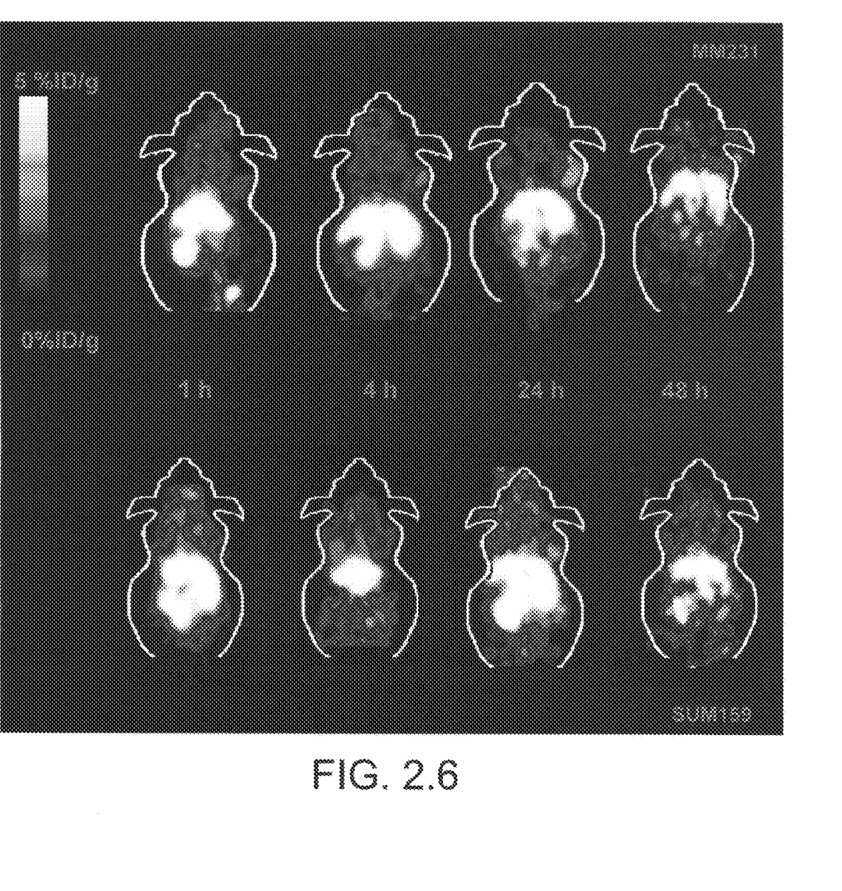

FIG. 2.6 illustrates the decay corrected coronal microPET images of a nu/nu mouse bearing MDA-MB-231 (Top) or SUM159 (Bottom) after tail vein injection of $^{64}$Cu-DOTA-CYS-$Z_{EGFR:1907}$, which illustrates another example of a breast cancer animal model.

CONCLUSIONS

EGFR affibody based PET imaging can successfully profile EGFR expression of TNBC in vivo.

REFERENCES FOR EXAMPLE 2

1. Friedman M, Orlova A, Johansson E, et al. Directed evolution to low nanomolar affinity of a tumor-targeting epidermal growth factor receptor-binding affibody molecule. Journal of molecular biology 2008; 376: 1388-402
2. Friedman M, Stahl S. Engineered affinity proteins for tumour-targeting applications. Biotechnology and applied biochemistry 2009; 53: 1-29
3. Miao Z, Ren G, Liu H, Jiang L, Cheng Z. Small-animal PET imaging of human epidermal growth factor receptor positive tumor with a 64Cu labeled affibody protein. Bioconjugate chemistry; 21: 947-54.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

We claim at least the following:

1. A method of detecting the over-expression of epidermal growth factor receptor (EGFR) in a subject, comprising:
   administering to the subject a $^{18}$F-FBEM-CYS-$Z_{EGFR:1907}$ probe, wherein $^{18}$F-FBEM is N-2-(4-$^{18}$F-fluorobenzamido)ethyl-maleimide), wherein $Z_{EGFR:1907}$ is SEQ ID NO: 1, and CYS is cysteine;
   imaging at least a portion of the subject; and
   detecting the $^{18}$F-FBEM-CYS-$Z_{EGFR:1907}$ probe, wherein the location of the $^{18}$F-FBEM-CYS-$Z_{EGFR:1907}$ probe corresponds to the over-expression of the EGFR.

2. A method of diagnosing the presence of a cancer or tumor in a subject comprising:
   administering to the subject a $^{18}$F-FBEM-CYS-$Z_{EGFR:1907}$ probe, wherein $^{18}$F-FBEM is N-2-(4-$^{18}$F-fluorobenzamido)ethyl-maleimide), wherein $Z_{EGFR:}$1907 is SEQ ID NO: 1, and CYS is cysteine;
imaging at least a portion of the subject; and
detecting the $^{18}$F-FBEM-CYS-$Z_{EGFR:1907}$ probe, wherein the location of the $^{18}$F-FBEM-CYS-$Z_{EGFR:1907}$ probe corresponds to the over-expression of the EGFR, wherein over-expression of EGFR corresponds to a cancer or tumor.

3. A method of diagnosing the presence of a cancer or tumor in a sample comprising:
contacting or administering to the sample a $^{18}$F-FBEM-CYS-$Z_{EGFR:1907}$ probe, wherein $^{18}$F-FBEM is N-2-(4-$^{18}$F-fluorobenzamido)ethyl-maleimide), wherein $Z_{EGFR:}$1907 is SEQ ID NO: 1, and CYS is cysteine;
imaging at least a portion of the sample; and
detecting the $^{18}$F-FBEM-CYS-$Z_{EGFR:1907}$ probe, wherein the location of the $^{18}$F-FBEM-CYS-$Z_{EGFR:1907}$ probe corresponds to the over-expression of the EGFR, wherein over-expression of EGFR corresponds to a cancer or tumor.

4. A method of monitoring the progress of a cancer or tumor in a subject comprising:
contacting or administering to the subject a $^{18}$F-FBEM-CYS-$Z_{EGFR:1907}$ probe, wherein $^{18}$F-FBEM is N-2-(4-$^{18}$F-fluorobenzamido)ethyl-maleimide), wherein $Z_{EGFR:1907}$ is SEQ ID NO: 1, and CYS is cysteine;
imaging at least a portion of the subject; and
detecting the $^{18}$F-FBEM-CYS-$Z_{EGFR:1907}$ probe, wherein the location of the 18F-FBEM-CYS-$Z_{EGFR:1907}$ probe corresponds to the over-expression of the EGFR, wherein over-expression of EGFR corresponds to a cancer or tumor, wherein the size of the location is monitored over time.

5. A method of monitoring the progress of a cancer or tumor in a sample comprising:
contacting or administering to the sample a $^{18}$F-FBEM-CYS-$Z_{EGFR:1907}$ probe, wherein $^{18}$F-FBEM is N-2-(4-$^{18}$F-fluorobenzamido)ethyl-maleimide), wherein $Z_{EGFR:1907}$ is SEQ ID NO: 1, and CYS is cysteine;
imaging at least a portion of the sample; and
detecting the $^{18}$F-FBEM-CYS-$Z_{EGFR:1907}$ probe, wherein the location of the 18F-FBEM-CYS-$Z_{EGFR:1907}$ probe corresponds to the over-expression of the EGFR, wherein over-expression of EGFR corresponds to a cancer or tumor, wherein the size of the location is monitored over time.

6. A probe, comprising: a $^{18}$F-FBEM-CYS-$Z_{EGFR:1907}$ probe, wherein $^{18}$F-FBEM is N-2-(4-$^{18}$F-fluorobenzamido) ethyl-maleimide), wherein $Z_{EGFR:1907}$ is SEQ ID NO: 1, and CYS is cysteine.

7. A composition, comprising:
a $^{18}$F-FBEM-CYS-$Z_{EGFR}$-1907 probe, wherein $^{18}$F-FBEM is N-2-(4-$^{18}$F-fluorobenzamido)ethyl-maleimide), wherein $Z_{EGFR:1907}$ is SEQ ID NO: 1, and CYS is cysteine.

8. A pharmaceutical composition, comprising:
a pharmaceutical carrier and an effective dose of a $^{18}$F-FBEM-CYS-$Z_{EGFR:1907}$ probe, wherein $^{18}$F-FBEM is N-2-(4-$^{18}$F-fluorobenzamido)ethyl-maleimide),
wherein $Z_{EGFR:1907}$ is SEQ ID NO: 1, and CYS is cysteine.

* * * * *

UNITED STATES PATENT AND TRADEMARK OFFICE
CERTIFICATE OF CORRECTION

PATENT NO. : 8,753,605 B2
APPLICATION NO. : 13/199428
DATED : June 17, 2014
INVENTOR(S) : Zhen Cheng et al.

It is certified that error appears in the above-identified patent and that said Letters Patent is hereby corrected as shown below:

In the Specification

Please delete the following text at column 1, lines 17-20 under the heading "Statement of Governmental Support":

"This invention was made with government support under grant number P50 CA114747, awarded by the National cancer institute of the United States government. The government has certain rights in the invention."

And replace with the following:

--This invention was made with Government support under contract CA114747 awarded by the National Institutes of Health. The Government has certain rights in the invention.--

Signed and Sealed this
Twenty-fourth Day of November, 2015

Michelle K. Lee
*Director of the United States Patent and Trademark Office*